United States Patent
Becker et al.

(10) Patent No.: US 11,304,842 B2
(45) Date of Patent: *Apr. 19, 2022

(54) OSTOMY BASE PLATE AND A METHOD OF APPLYING AN OSTOMY BASE PLATE

(71) Applicant: Coloplast A/S, Humlebaek (DK)

(72) Inventors: Kim Becker, Hilleroed (DK); Niels Pinholt, Roskilde (DK)

(73) Assignee: Coloplast A/S, Humlebaek (DK)

( * ) Notice: Subject to any disclaimer, the term of this patent is extended or adjusted under 35 U.S.C. 154(b) by 420 days.

This patent is subject to a terminal disclaimer.

(21) Appl. No.: 16/411,165

(22) Filed: May 14, 2019

(65) Prior Publication Data
US 2019/0262166 A1    Aug. 29, 2019

Related U.S. Application Data

(63) Continuation of application No. 15/105,609, filed as application No. PCT/DK2014/050436 on Dec. 17, 2014, now Pat. No. 10,335,309.

(30) Foreign Application Priority Data

Dec. 18, 2013 (DK) .......................... PA 2013 70787

(51) Int. Cl.
A61F 5/443    (2006.01)
A61F 5/448    (2006.01)
A61F 5/445    (2006.01)

(52) U.S. Cl.
CPC .............. *A61F 5/443* (2013.01); *A61F 5/445* (2013.01); *A61F 5/448* (2013.01); *A61F 2005/4483* (2013.01)

(58) Field of Classification Search
CPC .......... A61F 5/443; A61F 5/445; A61F 5/448; A61F 2005/4483
See application file for complete search history.

(56) References Cited

U.S. PATENT DOCUMENTS

| | | | |
|---|---|---|---|
| 8,740,988 B1* | 6/2014 | Hively | A61F 5/0076 623/23.65 |
| 2011/0152987 A1* | 6/2011 | Wahlgren | A61N 1/0492 607/115 |
| 2014/0276526 A1* | 9/2014 | Luce | A61F 13/02 604/393 |

FOREIGN PATENT DOCUMENTS

| | | |
|---|---|---|
| GB | 2509752 A | 7/2014 |
| JP | 2007105474 A | 4/2007 |

* cited by examiner

*Primary Examiner* — Adam Marcetich
(74) *Attorney, Agent, or Firm* — Coloplast Corp., Coloplast A/S; Nick Baumann

(57) ABSTRACT

A method and a device are described for an ostomy base plate having a storage configuration as delivered to a user and a use configuration as applied to skin of the user. In the storage configuration, a proximal side of the ostomy base plate is substantially convex, and in the use configuration, the proximal side of the ostomy base plate is substantially concave.

15 Claims, 5 Drawing Sheets

OSTOMY BASE PLATE AND A METHOD OF APPLYING AN OSTOMY BASE PLATE

The invention relates to an ostomy base plate. In particular, the invention relates to an adaptable ostomy base plate for ostomies or stomas located on a bulge or hernia on the skin surface of a user.

BACKGROUND

In connection with surgery for a number of diseases in the gastro-intestinal tract, one of the consequences in many cases is that the patient is left with an abdominal stoma, such as a colostomy, an ileostomy or a urostomy in the abdominal wall for the discharge of visceral contents. The discharge of visceral contents cannot be regulated at will. For that purpose, the user will have to rely on an appliance to collect the material emerging from such opening in a bag, which is later emptied and/or discarded at a suitable time.

An ostomy appliance may be in the form of a one-piece appliance for which a collecting bag for human body wastes is permanently, or fixedly, secured to an adhesive base plate for attachment to the human skin. Alternatively, the ostomy appliance may be a two-piece appliance comprising a base plate and a collecting bag which may be coupled to and un-coupled from each other through a coupling means. This has the effect that the base plate does not need to be separated from the skin of the user as often as exchange of the collecting bag requires. The base plate may need only to be changed every third or fourth day depending on the user, whereas the collecting bag may be changed more than once per day. Typically, it is desirable to need as few exchanges of the base plate as possible in order to reduce the risk of skin complications.

One of the main concerns of ostomates using ostomy appliances having an adhesive base plate for attachment to the skin surrounding a stoma, and where a collecting bag is attached to the base plate for collecting stoma output, is that the ostomy adhesive attachment may be compromised resulting in leakage or even complete detachment of the ostomy appliance.

Numerous attempts have been made to solve this problem and even though some attempts have been partly successful, still there exist no products, which completely solve this problem.

One reason why this is so difficult to solve is the fact that stomas and peoples anatomy are very different. Different considerations need to be made for thin people than for larger people, for different skin types, for placement of the stoma, which may vary a lot from person to person, for scar tissue surrounding the stoma, for local irregular skin topography and combinations of all of the above.

Particularly in relation to persons suffering from hernia, i.e. the phenomenon that a bodily structure (e.g. the intestine) protrudes through a rupture in smooth muscle tissue surrounding it, experience shows that it is often very difficult to attach an ostomy appliance to the skin surface where the hernia is located in a manner that provides satisfactory protection against leakage from stomal fluids. It is not uncommon that the surgical procedure undertaken to make a stoma on a patient also results in a weakening of the muscle tissue of the stomach wall which may consequently lead to the formation of a hernia where the stoma is located on the skin surface (or close or adjacent to the stoma).

In some cases where the stoma is located on a hernia, an additional complication may occur as gravity forces the protruding intestines downward and consequently also force the involved skin surface downward. Thereby, a stoma located on the hernia may begin to "point" downward (i.e. towards the user's feet) depriving the user of direct visual contact with the stoma and/or the peristomal skin surface. This is of course a great disadvantage for users applying their product themselves (which is the great majority of users) since the risk of misalignment or improper positioning of the product is largely increased. As a consequence, in such cases leakage problems may occur much more frequently.

Moreover, a hernia is not a static phenomenon. It is almost certain never to take a perfect geometrical shape but instead often has a highly irregular topography. This may be caused by many factors such as conditions in the physical surroundings of the user, level of activity of the user and contents of the bowels at any given time, just to mention a few.

In addition to the formation of hernias, other physical conditions or pathologies may also mean or lead to irregular skin topography such as bulges or otherwise "hilly" stomach skin surface, the causes including e.g. trauma and/or obesity.

DESCRIPTION OF RELATED ART

US 2012/0323193 discloses a one-piece ostomy device where the ostomy pouch is coupled to the wafer by a radially outwardly extending coupling layer. The configuration of the wafer is flat.

U.S. Pat. No. 4,419,100 discloses an ostomy appliance where the coupling means for the ostomy pouch is coupled to the faceplate by a radially inwardly extending web, the web allowing limited floating action between the coupling and the faceplate.

SUMMARY OF THE INVENTION

The present invention provides a base plate to be used as part of or with an ostomy appliance. Particularly, the invention provides having one or more sections having a shape that can be adapted or physically altered from one shape to another in order to both assist the user in applying the base plate in an easier manner and to achieve a better fit to the body. The base plate is especially advantageous to be used on users suffering from and having their stoma located on a non-planar and non-regular skin surface. The base plate is provided with coupling means for attaching a collection bag.

DETAILED DESCRIPTION OF THE INVENTION

Figure 1:
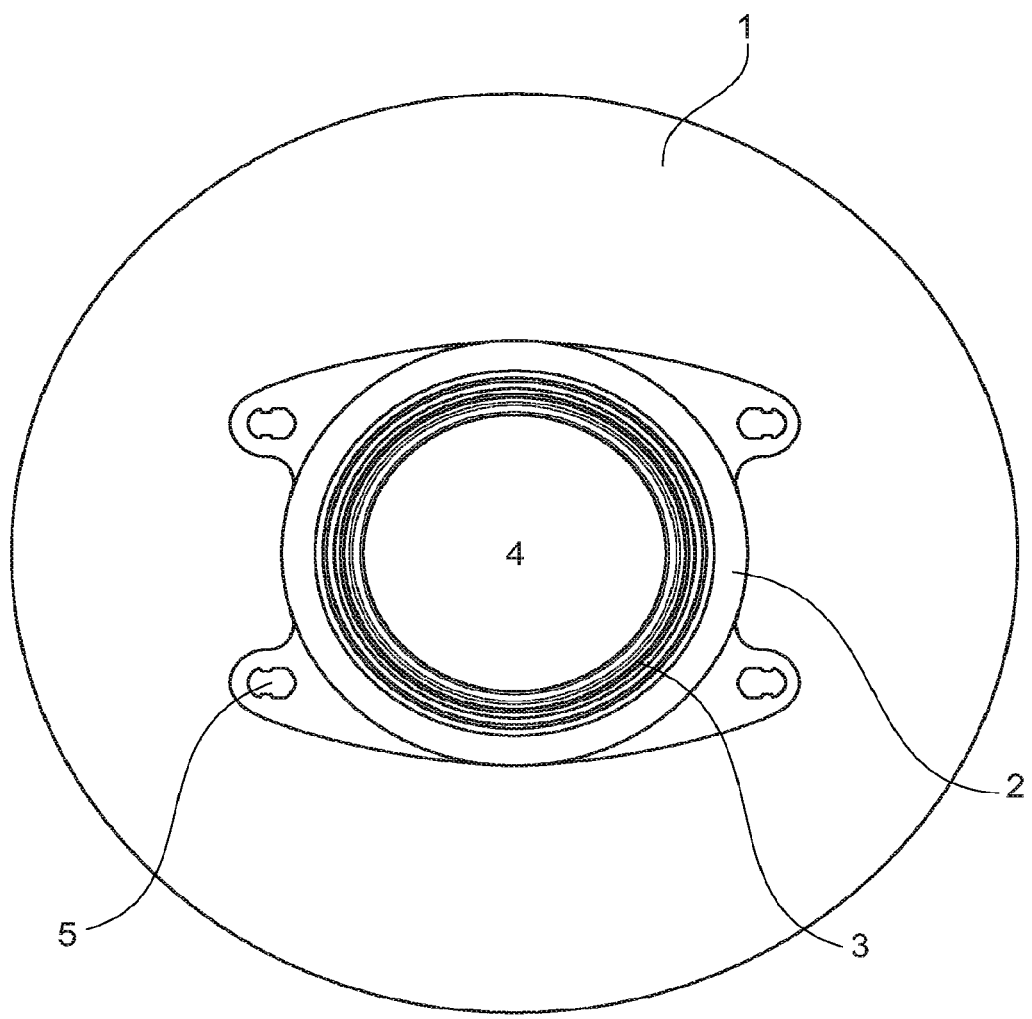
FIG. 1 is a schematic distal view of an ostomy base plate according to embodiments of the invention.

For interpretations in the context of the present application, some definitions regarding the subject matter of the attached claims are presented below.

When referring to the proximal side of a device or part of a device, the referral is to the skin-facing side, when the ostomy appliance is worn by a user. Likewise, whenever referring to the distal side of a device or part of a device, the referral is to the side facing away from the skin, when the ostomy appliance is worn by a user. In other words, the proximal side is the side closest to the user, when the appliance is fitted on a user and the distal side is the opposite side—the side furthest away from the user in use.

The axial direction, or axially, is defined as the direction of the stoma when the appliance is worn by a user. Thus, the axial direction is substantially perpendicular to the abdominal surface of the user.

The radial direction, or radially, is defined as transverse to the axial direction that is transversely to the direction of the stoma.

An "adaptable ostomy base plate" is intended to define that at least a part of the ostomy base plate can change its form or shape by an intended interaction of a user or health care professional.

A "flexible top film" is intended to define a film material carrying or having disposed thereon, adhesive material to make the product adhere to the skin of a user and that the top film material does not break or become weaker even at very high elongation or stretching rates. A flexible top film is further defined below.

An "elastic skin-friendly adhesive" is intended to define an adhesive material having a low risk of irritating the skin of a user and that the adhesive material is capable of following the elongations and relaxations of the flexible top film without breaking or substantially changing characteristics. An elastic skin-friendly adhesive is further defined below.

An "adhesive wafer" is intended to define a top film coated on the proximal surface with a skin-friendly adhesive.

A "substantially convex shape" is intended to define that an element or its corresponding surface has a shape or form that provides an overall convexity. In other words, while a smaller section or zone making up part of the overall element or its corresponding surface may have e.g. a linear shape or form, the element or surface as a whole has a convex shape. It is of course to be understood that if for a sheet- or plate-like element one major surface has a convex shape, the opposite major surface may necessarily have a corresponding concave shape. However, for clarification purposes only, and in relation to the present application, "convex" may preferably refer to the proximal side and "concave" to the distal side as both defined above.

Similarly, a "substantially concave shape" is intended to define that an element or its corresponding surface has a shape or form that provides an overall concavity.

"Initial engagement" is intended to define the first contact between the ostomy base plate and the skin surface of the user in the process of applying the product; however not meaning that the ostomy base plate is fully and functionally correct attached to the skin surface.

"Permanent engagement" is intended to define the engagement or attachment of the ostomy base plate when the application process is completed and the ostomy base plate is fully and functionally correct attached to the skin surface. However, it should be understood that permanent engagement is only intended to mean for the normal life- or wear time of the ostomy base plate.

"Release liner" is intended to define a liner covering the proximal (skin contacting) side of the skin-friendly adhesive, that ensures at least that the properties of the adhesive are preserved and that the adhesive surface is not laid open until just before the use.

"Fittingly engage" is intended to define that the attachment between the ostomy base plate and the skin surface is as good as possibly feasible and at least with no or only insignificant creases or folds on the proximal surface of the base plate.

"Peristomal skin surface" is intended to define an area of the skin surface adjacent to and surrounding the stoma. The extent of the area may be considered to correspond approximately to a skin surface area covered by at least a first section of the ostomy base plate—the first section then being closer to the stoma than a second section.

"Invertible" is intended to define that the at least first and/or second section provides little or no resistance to being shifted from a substantially convex shape to a substantially concave shape, or vice versa, by a movement involving no sudden switching or "flipping-over" of the section (i.e. as it is known from a bi-stable construction which may change shape when a certain force-threshold is reached).

"Store configuration" is intended to describe the position of the base plate before application is completed. The base plate is stable in this configuration and can be stored in this configuration. In the initial steps of application, the base plate may be in store configuration.

"Use configuration" is intended to describe the position of the base plate after application is completed, and is the inverted configuration of the store configuration. The coupling means are forced into close contact with the base plate in this configuration.

In a first aspect, the invention relates to an adaptable ostomy base plate comprising a flexible top film and having at least a first section, at least a first elastic skin-friendly adhesive on a proximal surface of said flexible top film, a stoma-receiving through-going hole in said first section, said first section being adjacent to and extending radially from said through-going hole, at least said first section has a first substantially convex shape for initial engagement with a peristomal skin surface, at least said first section being invertible to a first substantially concave shape to fittingly engage said first section to a topography of the peristomal skin surface for permanent engagement thereto, the base plate further comprising distally first coupling means for coupling engagement with corresponding coupling means on a collecting bag for human body wastes, the coupling means being radially to the hole, the first coupling means being attached to an inner periphery of a radially outwards extending connecting element and an outer periphery of the connecting element is attached to the top film, wherein the connecting element has a substantially concave shape.

The connecting element comprises an inner periphery for connection with the coupling means, a middle portion being unattached to the top film and the connecting element and an outer periphery being connected to the top film. Thus, the connecting element is only attached at is peripheral portions, which allow flexibility during application of the base plate and decreases the risk of deformation of the base plate during storage. The concave shape of the connecting element may elevate the coupling means with regard to the top film when this is in store configuration.

The coupling means may be in the form of a mechanical coupling or it may be an adhesive coupling.

The base plate may have any suitable shape, such as a substantially circular or oval outline.

The radius of the outer periphery of the connecting element is larger than the radius of the inner periphery. The outer periphery may have a radius being at least 1 mm, such as 2 mm, 3 mm, 4 mm, 5 mm, 6 mm, 7 mm, 8 mm, 9 mm or even 10 mm larger than the radius of the inner periphery of the connecting element. In one embodiment the radius of the outer periphery of the connecting element is between 1-20 mm, such as 1-15 mm, such as 2-15 mm, such as 5-15 mm, such as 2-10, such as 3-6, such as 5-10 mm or even 1-5 mm.

The connecting element may be in the form of a polymer film or a web. The connecting element may be flexible enough to follow the base plate when it is inverted, but yet firm enough not to stretch due to forces induced by a filled collection bag. In one embodiment, the connecting element is a flexible film.

The connecting element may be integrated with the coupling means, for example being molded together with the coupling means, being a single unit.

A radially outwardly connecting element may divert pulling forces from the collection bag away from the peripheral portions of the base plate thereby decreasing the risk of the plate peeling off.

Furthermore, when the device is inverted from the initial convex configuration to the concave configuration, the outwardly connecting element will pull the coupling means tightly towards the base plate and the skin, thereby preventing the collection bag to fall forward.

The construction with the outwardly connecting element between the coupling means and the base plate stabilizes the collection bag with regard to the base plate but still provides flexibility during application.

The "central portion" of the top film being herein defined as the portion of the adhesive coated top film being bounded by the attachment line of the inner periphery of the connecting element.

The attachment line of the connecting element to the top film defines a horizontal plane being substantially parallel to the skin. The connecting element defines an angle to the plane of the attachment line being substantially equal to the angle defined by the central portion of the top film and the plane of the attachment line. By substantially equal is meant that the angles deviates less than 10 degrees from each other's.

In storage configuration the central portion of the top film is convex and the connection element is concave and free space may be left between the top film and the coupling means. When the base plate is inverted into use configuration, the coupling means will be pulled towards the central portion of the top film as both the top film and the connecting element is now concave.

In storage configuration, the coupling means may possess a certain flexibility with respect to the top film. When the base plate is inverted into use configuration during application, the coupling means will be dragged into close contact with the top film and be firmly fixed at this position. By "firmly fixed" is meant that the coupling means cannot be moved or displaced with regard to the top film. The connecting element may be stretched and further facilitate holding the connecting means firmly in place.

The distance along the central portion of the top film measured from one opposing attachment point along the outer periphery of the connecting means (the diameter of the attachment line) is substantially the same as the radial distance of the coupling means combined with the connecting means. By substantially the same is meant that the distances deviates less than 5%. The distance of the combined connecting means and coupling means may be slightly longer than the distance measured along the central portion of the top film from one opposing attachment point along the outer periphery of the connecting means in order to ensure that unwanted pulling forces may occur along the attachment line when the device is inverted into use configuration.

Due to the equal distances of the coupling means combined with connecting element and the central portion of the top film beneath these, the coupling means will be firmly held towards the top film—though not physically adhered or welded to the top film—when the base plate is inverted during application.

In a second aspect, the invention relates to an adaptable ostomy base plate comprising a flexible top film and having at least a first section, at least a first elastic skin-friendly adhesive on a proximal surface of said flexible top film, a stoma-receiving through-going hole in said first section, said first section being adjacent to and extending radially from said through-going hole, the base plate further comprising distally first coupling means for coupling engagement with corresponding coupling means on a collecting bag for human body wastes, the coupling means being radially to the hole, the first coupling means being attached to the base plate via a radially outwards extending connecting element, wherein at least said first section has a first substantially convex shape for initial engagement with a peristomal skin surface, at least said first section being invertible to a first substantially concave shape to fittingly engage said first section to a topography of the peristomal skin surface for permanent engagement thereto and wherein the coupling means are movable with respect to the top film when the base plate is in convex shape and unmovable when the base plate is in concave shape.

By the invention according to the first aspect, a number of advantageous effects are achieved. First of all, a user having a stoma located on a bulge or hernia, or on an otherwise "hilly" topographic skin surface, has improved control of the product application procedure.

This effect is at least partly achieved in the following manner: subsequent to removal of at least one release liner covering at least partly the first section, the user engages a part of the first section immediately adjacent the stoma-receiving through-going hole with the peristomal skin surface, whereby only a small area of the adhesive on the proximal surface of the flexible top film is engaged with the peristomal skin surface.

Thereby, the user is provided with the opportunity to correct the positioning of the ostomy base plate to a more suitable position in case of misalignment of the initial engagement without having engaged the whole of the proximal adhesive surface of the flexible top film with the skin surface. This may be particularly advantageous in cases where the user has limited or no visual contact with the stoma.

Furthermore, since at least the first section has a first substantially convex shape, a user reaching down to the stoma located on the bulge or hernia in order to apply the product will have improved tactile and/or visual contact with the stoma and/or the peristomal area. This is because the part of the first section not initially engaging the peristomal skin surface extends away from the skin surface, thus leaving some space between the base plate and the skin, giving room for one or more of the user's fingers, and thereby the first section also does not block or impede possible visual contact for correct positioning of the base plate in relation to the stoma.

Once the initial engagement of the first section is effected, the invertible first section is inverted by the user to a first substantially concave shape so as to fittingly engage the first section with the peristomal skin surface on the bulge or hernia.

It is important to understand the manner in which this is done. Due to the flexibility of the flexible top film and the elasticity of the skin-friendly adhesive, the adhesive proximal side of the first section will adapt smoothly to the topography of the peristomal skin surface when the user applies a gentle pressure to the distal surface of the first section.

This may advantageously, but not exclusively, be done by the user letting his finger or fingers describe one or more radial motions by placing the finger(s) immediately adjacent the stoma, providing pressure to the distal surface, and sliding the finger gently across the distal surface of the first section radially away from the stoma. Alternatively, the adaptation may be done by a motion placing a finger immediately adjacent the stoma, providing pressure to the distal surface, and sliding the finger gently in a "spiral-like" pattern gradually away from the stoma over the entire distal surface of the first section.

However, regardless of the way of adaptation, at least the flexibility of the flexible top film and the elasticity of the skin-friendly adhesive along with the first substantially convex shape of the first section make the fitting engagement of the first section possible.

As can be understood from the above, the flexible top film and the elastic skin-friendly adhesive facilitate the inversion of the first section for application to the peristomal skin surface by a continuous, regular movement (or movements). This provides a user with improved control of the application procedure. This should be seen in contrast to a sudden movement which would be the case e.g. in the case of a bi-stable construction, i.e. a construction having one predetermined position where it changes shape from one form to another, e.g. from convex to concave.

When the base plate is inverted from the convex to the concave shape, the coupling means will be pulled towards the top film and lye firmly against this when the base plate is in inverted position. But due to the limited area of attachment, and the attachment being at a distance from the hole, the flexibility is high and the peeling effect is low.

The flexible top film according to the invention may be a blown film primarily based on one or more Ethylene Vinyl Acetate (EVA) materials, one or more thermoplastic polyurethane elastomer (TPU) based materials and one or more polyethylene (PE) materials. Particularly, but not exclusively, the EVA and TPU based materials may provide a good basis for engagement of the top film with other elements of the ostomy base plate such as the adhesive(s) and optional first coupling means, or in the case of the base plate being used for a one-piece ostomy appliance, with the material of the collecting bag for human body wastes. The PE material(s) may particularly, but not exclusively, provide a suitable basis for shaping the flexible top film into a convex or concave shape to be able to fittingly engage with a topography of a user's skin surface.

In embodiments, the flexible top film is a three-layer laminate.

Particularly, but not exclusively, the flexible top film may be made as a laminate comprising three individual (blown) layers each of which is made from either EVA, TPU or PE or from a blend of these. In the three-layer laminate, the distal-most (with reference to the use situation of the ostomy base plate) layer may be made from a blend of Elvax® 3190, an EVA material from DuPont, and Orevac® 18360, a PE material from Arkema; the middle layer may be made from a blend of Elvax® 3190, Elastollan® 890, a TPU-Polyester material from BASF and Elastollan® 978, another TPU-Polyester material from BASF and; the proximal layer may also be made from a blend of Elvax® 3190, Elastollan® 890 and Elastollan® 978. In addition to these components each of the distal and proximal layers of the three-layer laminate may also comprise a minor amount of slip agent (to assist when unrolling the top film material for production of the ostomy base plate). The slip agent may be a PE/EVA polymer carrier containing silica, oleamid (fatty acid oleic acid) and erucamide (monounsaturated omega-9 fatty acid), such as Polystatic® 90200-2. The silica and the ole-/erucamides in the slip agent provide the slipping effect.

The overall thickness of the flexible top film may be in a range of 30-70 µm, such as 35-50 µm, such as approximately 40 µm. In embodiments of the three-layer laminate, each individual layer may have a thickness of at least 10 µm for ease of production of the individual layers.

The flexible top film may be stretched prior to being used in the production of the ostomy base plate. This will provide a pre-tensioning or bias in the flexible top film. The flexible top film may be stretched radially in all directions to obtain the same bias in all directions of the plane thereof. This pre-tensioning or bias in the flexible top film incurs additional flexibility to the flexible top film. Particularly, it may improve the film's ability to adapt to a certain shape in a shaping process.

The flexible top film may have a flexibility measured as a percentage of elongation of the flexible top film material before it fails (considered as the point where plastic deformation of the flexible top film occurs). The flexible top film may be 250-700% elongatable, such as 300-600% elongatable, such as 350-450% elongatable, such as 400% elongatable before failure.

The first elastic skin-friendly adhesive according to the invention may be a pressure sensitive adhesive composition suitable for medical purposes comprising a rubbery elastomeric base and one or more water soluble or water swellable hydrocolloids, the adhesive composition comprising a substantially homogeneous mixture of 25-60% of one or more polyisobutylenes, 3-35% of one or more styrene copolymers, and 20-60% of one or more hydrocolloids, wherein the percentage by weight of one or more polyisobutylenes and one or more styrene copolymers and one or more hydrocolloids add up to 100% by weight of the adhesive composition. For further information on such compositions reference is made to applicant's granted European patent EP1541180B1.

The thickness of the first elastic skin-friendly adhesive layer may be in a range of 1-2 mm, corresponding to 1000 µm-2000 µm, such as 1200 µm-1800 µm, such as 1400 µm-1600 µm.

For the production of the ostomy base plate, the following is an example of manufacture: first the adhesive(s) is/are provided on the proximal surface of the flexible top film and thereafter the at least one release liner is provided on the adhesive surface. At least the first section of the planar laminate blank is then subsequently placed in a vacuum-forming machine, the moulding tool having the relevant convex form. Heating means, such as a radiant heat source is placed in connection with the vacuum-forming machine in order to soften the laminate blank, and the laminate blank is subjected to heat and vacuum forming for an adequate holding time. Alternatively, the laminate blank may also be manufactured by means of a heat and pressure die or indeed any other suitable procedure.

In embodiments where the second section of the ostomy base plate is also convex shaped (or concave shaped) the moulding tool used in the process described above may be configured to provide both convex shapes (or convex shape of the first section and concave shape of the second section). Alternatively, the shaping process may be divided into more steps, e.g. first shaping the first section and separately shaping the second section. The stoma-receiving through-going hole may be cut in the ostomy base plate before or after the shaping process.

Due to its elasticity, the first skin-friendly adhesive may easily adapt to the convex shape of at least the first section together with the flexible top film and the at least one release liner in the shaping process. Indeed, subjected to the above described shaping process, at least the first section of the ostomy base plate according to the invention initially always has the convex shape notwithstanding its high degree of adaptability. As mentioned, this may be seen in contrast to e.g. the known bi-stable convex ostomy products that are relatively rigid and only adaptable in an "either inverted/not inverted" sense.

The at least one release liner used in connection with the ostomy base plate according to the invention, may suitably be a siliconised or fluorinated liner, such as a siliconised or fluorinated craft paper, polyethylene, polypropylene or polyethylene terephthalate film.

In embodiments, the second section has a second substantially convex shape being invertible to a second substantially concave shape.

This may be particularly advantageous to further improve the tactile and/or visual contact with the stoma and/or the peristomal area. In such embodiments, where then both the first and the second sections initially extend away from the skin surface, there will be additional space between the base plate and the skin giving plenty of room for the user's manual handling of the base plate during application. Also, thereby the second section does not block or impede the user's visual contact with the stoma.

The second section may be inverted and permanently engaged to the skin surface of the user in the same or substantially similar manner as the first section and as described above. The engagement of the second section to the skin surface is generally carried out after the first section has been permanently engaged with the peristomal skin surface. However, in the case of a two-piece ostomy appliance, it may be advantageous to engage the second section to the skin surface of the user only after the collecting bag has been coupled to correct engagement with the ostomy base plate.

The second section surrounds the first section of the adaptable ostomy base plate. In embodiments, a transition between the first and the second section may be defined by a zone where the two convex sections meet at an angle to each other.

This may be particularly, but not exclusively, advantageous if easy distinction of the sections by the user is required, e.g. facilitating the user's following of instructions for use.

In other embodiments, the transition may be straight or smooth (i.e. no angle between the sections) thus ruling out at least any visual difference between the sections. If the first and second sections are arranged according to such embodiments there may be no difference between the convexity of the first and second section, thus the first and second section may be perceived, or actually manufactured, as a single "coherent" or integral convex section. This may be particularly relevant in relation to minimizing production costs.

Additionally, however, the first and the second section may have different convexities. This could by way of example be relevant in relation to different dimensions and/or sizes of the ostomy base plate.

In embodiments, the second section has a second substantially concave shape. This should be seen in contrast to the embodiments described above wherein the second section is invertible to a second substantially concave shape. Therefore, in these embodiments the second section has a pre-defined substantially concave shape. A transition between the first and second section is defined by a zone where the two sections meet at an angle to each other. Consequently, the initial substantially convex shape of the first section makes the first section extend away from the skin surface, while the substantially concave shape of the second section makes the second section extend toward the skin surface from the position of the transition between the sections.

In embodiments, the ostomy base plate according to the invention further comprises a substantially planar surface zone between said first and second sections.

"Substantially planar" is intended to define that a surface zone of the ostomy base plate has a linear or planar form close to parallel with a straight horizontal line; at least it is not inclined in relation to such horizontal line by more than +/−10 degrees. At least this definition is meant to clearly identify that the surface zone does not possess any kind of convex or concave shape in contrast to the first and second section.

The substantially planar surface zone between the sections may provide extra control with regard to the user's handling of the product in the application procedure and may further hinder that the first and/or the second sections become obstructive in e.g. the distal or proximal direction with regard to e.g. the user's clothes or with regard to other objects or other physical areas of contact on the user's body. This may be particularly, but not exclusively, efficient, if a relatively large adhesive area of the ostomy base plate is needed (e.g. for high-volume output collecting bags).

The substantially planar surface zone may form at least part of a first transition between the first section and the zone and/or form at least part of a second transition between the second section and the zone.

The first coupling means may be in the form of a mechanical coupling, comprising an annular ring having a flange or similar member extending axially away from the planar surface zone to engage with engaging second coupling means on a collecting bag such as a corresponding annular ring with a channel for receiving the flange. Alternatively, the coupling may be an adhesive coupling where the first coupling means may comprise a radially extending annular flange that provides a receiving surface for receipt of second coupling means on a collecting bag such as an annular adhesive flange. However, these are mere examples of typical coupling means for ostomy appliances; others types of engaging coupling means are not to be considered excluded.

The first coupling means are not directly joined to the substantially planar surface, but are joined through the connecting element to the surface by welding, heat laminating, gluing or other commonly known suitable joining procedures. The first coupling means are joined through means of the connecting element, for example in the form of a film material attached to the substantially planar surface at the outer periphery and to the first coupling means at the inner periphery.

In embodiments, the adaptable ostomy base plate comprises a second skin-friendly adhesive on the proximal surface of the flexible top film.

The second skin-friendly adhesive may be provided so as to give the proximal surface of the base plate different characteristics and/or effects. As an example, the second skin-friendly adhesive may comprise smaller or a larger amount of a moisture absorbing component such as hydrocolloids and/or be more or less adaptable than the first skin-friendly adhesive. The second skin-friendly adhesive may be provided in a single or in multiple zones or areas. The zones or areas may have particular suitable shapes or forms depending on the function or effect of the second skin-friendly adhesive.

In embodiments, the first elastic skin-friendly adhesive is provided on the first section and the second skin-friendly adhesive is provided on the second section.

This disposition of the first and second skin-friendly adhesive effectively provides an ostomy base plate wherein the first skin-friendly adhesive having one set of characteristics covers the peristomal area, and the second skin-friendly adhesive having another set of characteristics covers the skin surface around (radially beyond) the peristomal skin surface.

In embodiments, the second skin-friendly adhesive is elastic. This means, that in addition to the first elastic skin-friendly adhesive, also the second skin-friendly adhesive has elastic properties. The second skin-friendly adhesive may be more or may be less elastic than the first elastic skin-friendly adhesive or the two adhesives may even have identical elasticities if desired.

Where the elasticity of a construction is typically measured by the tensile elasticity Modulus (E) (also known as Young's Modulus) the elasticity of an adhesive is typically measured by the shear Modulus (G).

The shear Modulus of a viscoelastic material like an adhesive can be divided into a viscous part called the Loss Modulus (G") and an elastic part called the Storage Modulus (G'). The elastic response of the adhesives can therefore be measured by measuring G' by dynamic mechanical analysis (DMA), which is a well-known and established procedure to a skilled person working in the field of adhesives.

Body movements according to normal daily life routines typically occur at frequencies around 1-10 Hz. At these frequencies, the G' of the first elastic skin-friendly adhesive may be in a range from 850-1200 MPa, whereas G' of the second elastic skin-friendly adhesive may be in a range from 40-80 MPa.

In embodiments, the second elastic skin-friendly adhesive comprises a polar plasticising oil or a combination of polar plasticising oils in the content of above 10% (w/w) of the final second adhesive, and at least one polar polyethylene copolymer, wherein the content of the polyethylene copolymer is 10-50% (w/w) of the final second adhesive, the polyethylene copolymer has a melt flow index below 2 g/10 min (190° C./21.1 N).

Polymers that may be used for the second skin-friendly adhesive will generally be copolymers of ethylene and a polar monomer. The copolymers typically comprise less than about 70% ethylene, have water vapour transmission of more than 50 $g/m^2/day$ and a melt flow index of less than 2 g/10 min (190° C./21.1 N). The melt flow index can be measured by the methods given in ISO 1133 and ASTM D1238. Examples of such polymers are copolymers of ethylene and vinyl acetate and copolymers of ethylene and butyl acrylate. Particularly preferred is ethylene and vinyl acetate copolymers with more than about 40% (w/w) vinyl acetate, a melt flow index of less than 2 g/10 min (190° C./21.1 N), and a water vapour transmission of more than 50 $g/m^2/day$ for a 150 µm sheet when measured according to MVTR Test Method (inverted cup method).

Polar oils, which may be used in the invention, will generally be those that have good solubility in the polar domains of the polymer, i.e. provide softness without sacrificing too much tensile strength of the polymer. Oils that can support good water vapour permeability are preferred. Examples of such oils are vegetable and animal oils and derivatives thereof. Preferred polar oils are esters, ethers and glycols and particularly preferred is Poly Propylene Oxide, e.g. alpha-butoxy-polyoxypropylene.

Further information on the types of adhesives suitable for the second skin-friendly adhesive disclosed in these embodiments is available in applicant's published application WO 2009/006901A1.

In embodiments, the thickness of the second elastic skin-friendly adhesive is 300-700 µm, such as 550-650 µm, such as 600 µm.

Particularly, when using the above defined polyethylene copolymer based adhesive as the second elastic adhesive in the thickness of 300-700 µm a flexible and soft adhesive base plate which can be handled without a stiffening, or stabilizing, layer is achieved. For further information on the combination of such a thickness range and the defined polyethylene copolymer, reference is made to applicant's published application WO 2012/022352A1.

In embodiments, at least the second section further comprises a reinforcing element. Thereby, the second section may be easier to handle because it is at least partly stiffened or stabilized by the reinforcing element. Particularly in the case of a relatively large (diameter) ostomy base plate according to the invention this may help the user to control the product. By way of example, the reinforcing element could be a permeable or perforated film layer such as of a blown film but also including non-wovens or foamed film layers. The reinforcing element may be embedded in the second skin-friendly adhesive or located between the distal surface of the adhesive and the proximal surface of the flexible top film.

DETAILED DESCRIPTION OF THE DRAWING

Initially, it shall be noted that the figures are schematic illustrations intended only to address the principles and functions of the base plate according to the invention and are not to be considered limiting to the scope of the attached claims. Furthermore, the figures and particularly the individually illustrated elements are not necessarily to scale, neither individually nor in relation to each other.

FIG. 1 shows an adaptable ostomy base plate seen from the distal side according to embodiments of the invention. The base plate comprises a flexible top film (1) coated on the proximal surface with a skin friendly adhesive. The distal surface of the base plate comprises coupling means (3) for attachment to a collecting bag (not shown). The coupling means (3) are connected to the top film (1) through an outwards extending element (2), extending from the coupling means (3) and radially outwards. The central portion is provided with a hole (4) for accommodating a stoma. The base plate may optionally be provided with means for attaching a belt (5).

Figure 2:
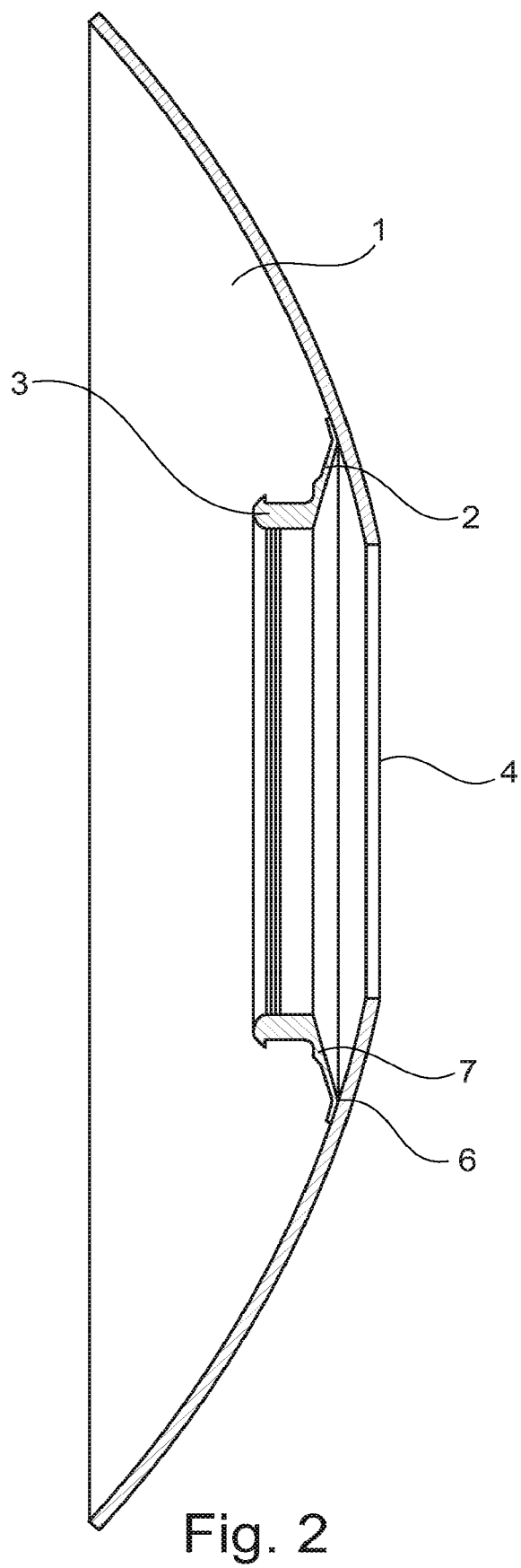
FIG. 2 is a schematic cross-sectional view of an ostomy base plate in storage configuration, according to embodiments of the invention.

FIG. 2 shows an embodiment corresponding to the one of FIG. 1, but without means for attachment of a belt, in cross-section, in a convex configuration for storage and application. The inner periphery (7) of the connecting element (2) is attached to the coupling means (3) and the outer periphery (6) is attached to the top film (1). Thus, the coupling means (3) are not connected directly to the top film (1) but are connected via the intermediate connecting element (2). The coupling means (3) shown in this embodiment is a mechanical coupling. The coupling means comprises a first part extending distally from the device and a "second part extending radially and substantially perpendicularly from the first part and being attached or integrated with the connecting element.

The connecting element (2) is only attached at its inner and outer periphery (7,6); whereas the middle portion between the inner and outer peripheries (7,6) remains unattached. The adhesive coated top film (1) defines a convex shape, like a cup or bowl or a section of a sphere, extending in distal direction. This enables the base plate to be positioned correctly around the stoma without bringing the entire adhesive surface of the top film (1) in contact with the surrounding skin. The connecting element is concave; thereby lifting the coupling means a distance away from the central portion of the top film.

Figure 3:
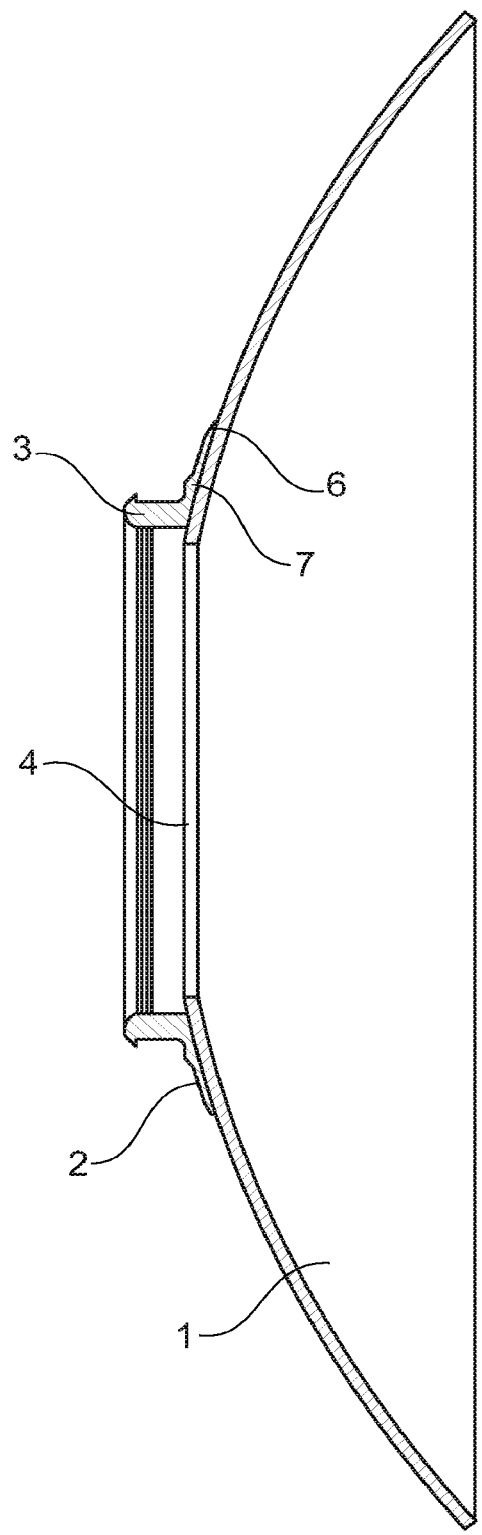
FIG. 3 is a schematic cross-sectional view of the ostomy base plate in FIG. 2 in use configuration, placed on the skin surface of a user.

When the base plate has been correctly positioned around the stoma, the base plate (1) is inverted into a concave configuration as shown in FIG. 3 and the remaining adhesive surface is attached to the peristomal skin. When the base plate (1) is inverted, the coupling means (3) will be pulled towards the wafer and held tight in close contact with the top film. In this position, the movability of the coupling means (3) with regard to the top film is limited, and prolapse of the coupling means (3) is avoided. A collection bag (not shown) may then be attached to the base plate (1) via the coupling means (3).

Figure 4:
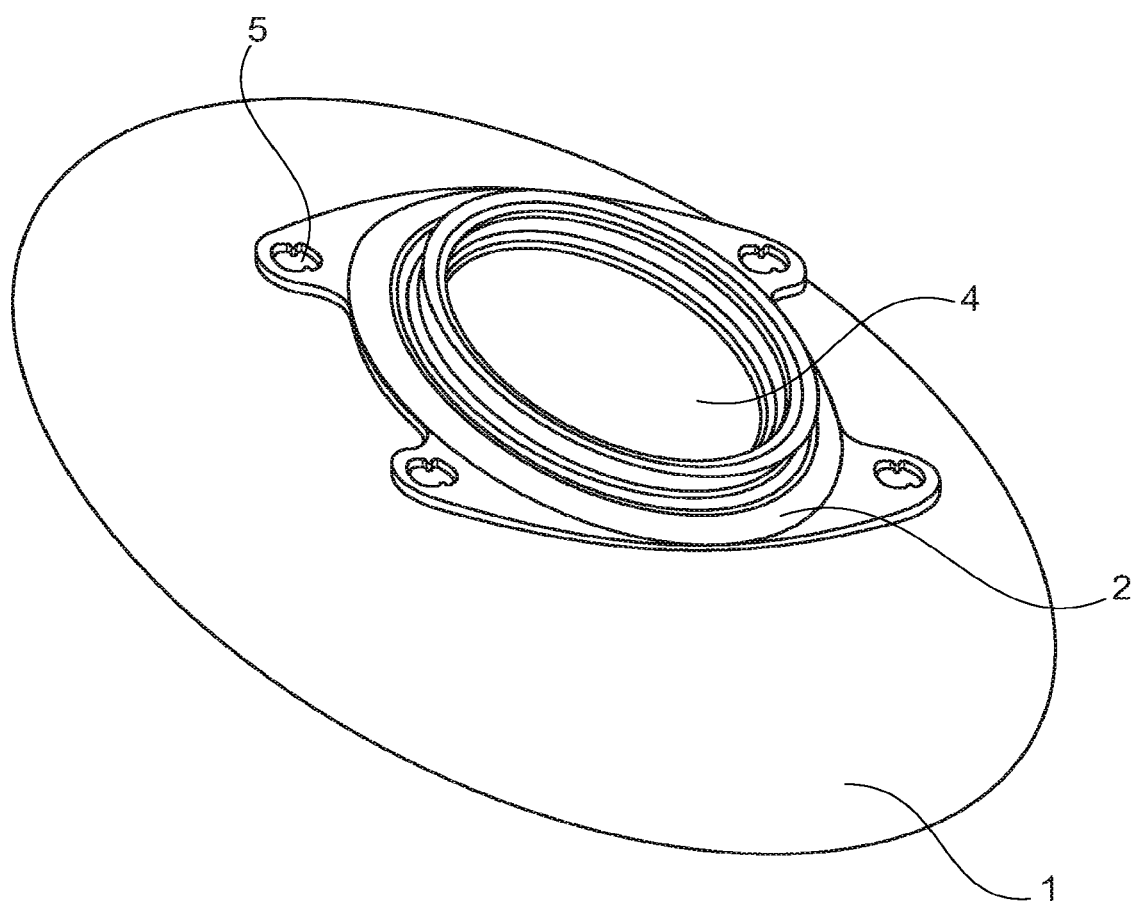
FIG. 4 is a schematic isometric view of an ostomy base plate according to the embodiments introduced in FIG. 1 shown in use configuration.

FIG. 4 shows a perspective view of the base plate (1) in the concave use configuration.

Figure 5:
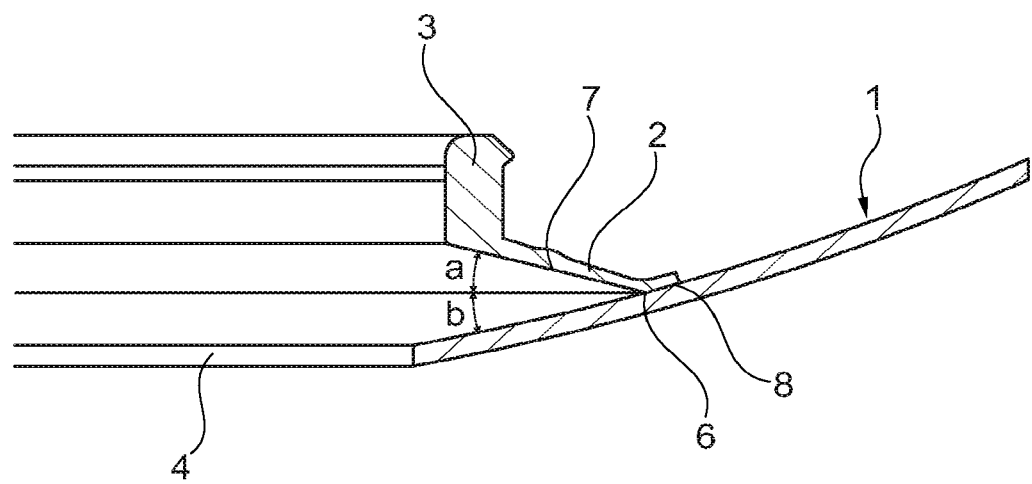
FIG. 5 is an enlarged view of a section of FIG. 2.

FIG. 5 shows an enlarged view of the connecting element (2) in storage configuration. The coated top film of the base plate (1) defines a convex cup shape. The coupling means (3) may be spaced apart from the top film but connected via the connecting element (2). The connecting element (2) is attached to the top film by a section (8) being substantially parallel to the top film. If the coupling means (3) had been directly attached to the top film, the flexibility or the device would have been lower as well as the coupling means (3) may have deformed the base plate, due to the force induced at the attachment zone.

The connecting element (2) is extending from the attachment line along the outer periphery (6) and inwardly towards the inner periphery (7) being attached to the coupling means (3), the connecting element (2) thereby defining concave shape in the form of a line or slightly curved line. The connecting element may define a shape corresponding substantially to a mirror image of the underlying central portion of the top film. In this way, the radial distance of the top film, measured from one opposing attachment point of the outer periphery of the connecting means to another is substantially the same as the radial distance of the coupling means combined with the connecting means. By substantially the same is meant that the distances deviates less than 5%.

As can be seen from FIG. 5, showing an enlarged view of a cross-section of FIG. 2, the connecting element (2) defines an angle (a) with the plane of the outer periphery (6) of the connection element. The base plate under the coupling connection element forms an angle (b) with the plane of the outer periphery of the connection element. If the angle (a) is substantially larger than the angle (b), the coupling means may not be totally fixed when inverted, but may be able to move more or less with respect to the base plate as well as the bag may prolapsed from the body when filled, which is undesired. However, the angle a may be slightly larger than the angle b without compromising the fixation of the connecting means in the case of a thick layer of adhesive.

If the angle (a) is substantially smaller than angle (b), the base plate may be deformed at the attachment line due to the forces from the coupling means during store position dragging the attachment line inwards, as well as excessive stress and tension will be introduced when the base plate is inverted.

The connecting element may be flexible and/or elastic it may cope for angle (a) being slightly smaller than angle (b).

The invention claimed is:

1. An ostomy base plate having a storage configuration as delivered to a user and a use configuration as applied to skin of the user, the ostomy base plate comprising:
   a film with a hole formed through the film, where the hole is adapted for placement around a stoma of the user;
   adhesive applied around the hole on a proximal side of the film; and
   a coupling connector secured to a distal side of the film, the coupling connector including a connecting element having an outer periphery connected to the distal side of the film and an intermediate bridge extending from the outer periphery to a coupling ring, where the coupling ring surrounds the hole formed through the film;
   wherein, in the storage configuration, the adhesive applied on the proximal side of the film is in a substantially convex shape with the intermediate bridge and the coupling ring spaced apart from the distal side of the film;
   wherein, in the use configuration, the adhesive applied on the proximal side of the film is in a substantially concave shape with the intermediate bridge and the coupling ring in contact with the distal side of the film.

2. The ostomy base plate of claim 1, wherein the coupling ring is adapted to couple with a waste collecting bag.

3. The ostomy base plate of claim 1, wherein the coupling ring is circular, and a diameter of the coupling ring is larger than a diameter of the hole formed through the film.

4. The ostomy base plate of claim 1, wherein the connecting element adapts the ostomy base plate to be invertible between the storage configuration and the use configuration.

5. The ostomy base plate of claim 1, wherein the connecting element adapts the ostomy base plate to fittingly engage with a topography of the skin of the user around an entire perimeter of the stoma.

6. The ostomy base plate of claim 1, wherein the coupling connector is attached to the distal side of the film only at the outer periphery of the connecting element.

7. The ostomy base plate of claim 1, wherein the connecting element is a film.

8. The ostomy base plate of claim 1, wherein the adhesive is elastic.

9. The ostomy base plate of claim 1, wherein the film is a three-layer laminate.

10. A method of applying an ostomy base plate, the method comprising:
    providing the ostomy base plate in a storage configuration presenting a proximal side of the ostomy base plate in a substantially convex shape;
    providing a coupling connector secured to a distal side of the ostomy base plate with a coupling ring of the coupling connector spaced apart from the distal side of the ostomy base plate;
    adhering a portion of an adhesive applied on the proximal side of the ostomy base plate to a peristomal skin surface and leaving a perimeter of the ostomy base plate spaced away from the peristomal skin surface; and inverting the ostomy base plate to a use configuration, and inverting the adhesive applied on the proximal side of the ostomy base plate to a substantially concave shape contacting skin of a user such that the coupling ring of the coupling connector touches the distal side of the ostomy base plate.

11. The method of claim 10, further comprising fittingly engaging the substantially concave shape of the proximal side of the ostomy base to topography of a hernia of the peristomal skin surface.

12. The method of claim 10, further comprising correcting a misalignment of the proximal side of the ostomy base plate to the peristomal skin surface by repositioning the portion of the adhesive applied on the proximal side of the ostomy base plate to an area of the peristomal skin surface.

13. The method of claim 10, further comprising instructing a user to move a finger in a radial motion along the distal side of the ostomy base plate and fittingly engaging the proximal side of the ostomy base plate onto a bulge in the peristomal skin surface.

14. The method of claim 10, further comprising attaching a waste collecting bag to the coupling ring of the ostomy base plate.

15. An ostomy base plate having a storage configuration as delivered to a user and a use configuration as applied to skin of the user, the ostomy base plate comprising:

a film with a hole formed through the film, where the hole is adapted for placement around a stoma of the user;

adhesive applied around the hole on a proximal side of the film; and a coupling connector secured to a distal side of the film, the coupling connector including a connecting element having an outer periphery connected to the distal side of the film and an intermediate bridge extending from the outer periphery to a coupling ring, where the coupling ring surrounds the hole formed through the film;

wherein, in the storage configuration, the adhesive applied on the proximal side of the film is in a substantially convex shape with the intermediate bridge and the coupling ring spaced apart from the distal side of the film;

wherein, in the use configuration, the adhesive applied on the proximal side of the film is in a substantially concave shape with the intermediate bridge and the coupling ring in contact with the distal side of the film;

wherein the adhesive is an elastic adhesive.

* * * * *

UNITED STATES PATENT AND TRADEMARK OFFICE
CERTIFICATE OF CORRECTION

| | | |
|---|---|---|
| PATENT NO. | : 11,304,842 B2 | Page 1 of 1 |
| APPLICATION NO. | : 16/411165 | |
| DATED | : April 19, 2022 | |
| INVENTOR(S) | : Becker et al. | |

It is certified that error appears in the above-identified patent and that said Letters Patent is hereby corrected as shown below:

In the Claims

1. In Column 15, Line 12, in Claim 11, delete "ostomy base to" and insert -- ostomy base plate to --, therefor.

Signed and Sealed this
Ninth Day of May, 2023

Katherine Kelly Vidal
*Director of the United States Patent and Trademark Office*